United States Patent [19]

Leisegang

[11] 4,134,637
[45] Jan. 16, 1979

[54] COLPOSCOPE WITH PHOTOGRAPHIC ATTACHMENT

[76] Inventor: Fritz Leisegang, Leibnizstrasse 32, D-1000 Berlin 12, Fed. Rep. of Germany

[21] Appl. No.: 777,822

[22] Filed: Mar. 15, 1977

[30] Foreign Application Priority Data

Dec. 13, 1976 [DE] Fed. Rep. of Germany ... 7639305[U]

[51] Int. Cl.² ............................................. G02B 21/00
[52] U.S. Cl. ......................................... 350/19; 350/36; 354/79
[58] Field of Search .............. 350/18, 14, 36; 354/79; 128/6

[56] References Cited

U.S. PATENT DOCUMENTS

| | | | |
|---|---|---|---|
| 2,209,532 | 7/1940 | Michel | 350/19 X |
| 2,737,079 | 3/1956 | Brown et al. | 350/19 X |
| 3,994,288 | 11/1976 | Stumpf | 350/19 X |

Primary Examiner—John K. Corbin
Assistant Examiner—Matthew W. Koren

[57] ABSTRACT

This new version concerns a Colposcope with Photographic-Attachment, wherein the Colposcope is equipped with two side by side oculars, two objective lenses in line with the oculars as well as a light source, reflected into the field of observation and a connecting-bush for the tube of the Photo-Attachment.

6 Claims, 3 Drawing Figures

COLPOSCOPE WITH PHOTOGRAPHIC ATTACHMENT

FIELD OF THE INVENTION

Colposcopes are primarily used by Gynecologists in their offices and in hospitals for observation of the vagina and cervix during examination and treatment.

BACKGROUND OF THE INVENTION

Of special significance is the magnified image in conjunction with a special light-source. The examiner looks through the oculars, similar as looking through a set of binoculars. The images are true to colour and not inverted. A large working distance permits manipulation and operative treatment in the illuminated area, during colposcopic examination. For a better concept of depth and space during manipulation, the Colposcopes are equipped with a Stereo-Lens-System. For documentation of important observations, or as a reminder for further treatment — especially treatment over long periods of time — it becomes necessary to record in some form, preferably in the form of a small colour picture, the observation made through the Colposcope. As the observations are made in stereo, the pictures are taken accordingly, to reproduce a stereo image.

Up to date, mainly colour-slides of mono - or stereo pictures were taken, which could be studied through special equipment, such as slide-projectors, or similar. Even polarized filter-systems for projection are used, where the observer is wearing a specially provided pair of spectacles. In addition, small compact viewers with a light-source give a good stereoscopic reproduction.

A very special attachment, between Colposcope and Camera, makes the labeling and marking of each individual picture possible while a picture is being taken.

Photos taken on negative — or positive — film, preferably small frames of 24 X 36mm, are taken on films of standard length, as sold and produced by the manufacturers, and, according to manufacturers specifications, cannot be altered. Developing the films, especially colour-slide films, is not possible in the doctors' office because they have to be processed in a proper laboratory.

Doctors, and in particular Gynecologists, who are using these pictures for either patient records or to be sent to a referring Physician, are restricted in their activities, because the time involved is too long, to complete a standard film, to have this film developed, framed and categorized. Mistakes which are made — e.g. — exposure too strong because the wrong diaphragm has been used or picture is unsharp — can only be discovered when the developed films are returned and there is no immediate possibility for correction.

In the new version, a Colposcope with Photographic Attachment is constructed in such a way, that the above listed disadvantages are eliminated and an Instant-Picture can be produced.

In the most recent construction for the Photographic Attachment, this task has been accomplished by mounting two side by side adjustable reflex mirrors in the range of the camera tube inside the Colposcope head, so that the light beam travels from the objective lens via the reflex-mirrors, through two side by side image relay objectives, onto two fixed reflex-mirrors, onto the projection area of the film-cassette.

Further details of the new version are as follows: This optical instrument consists of a stereoscopic projection unit for the observer of the object under examination, and, adjusted to the same focal distance, a photographic Camera-Attachment. On the photographic side of the Colposcope-Head, two pictures are projected onto the Camera-Attachment in the scale of 1:1 of the object under examination. The examiner looks through a set of binoculars. The area seen through the oculars is of exactly the same size as the area photographed. Accordingly, the area of the light available, is restricted by the optic of the light source. The optical system is a stereoscopic arrangement and gives a magnification of 12:1. A new system for a special camera has been added and fitted into the projection area of the normally used 24 X 36 film plane. This new attachment, using a further optical system, projects the picture from the existing focal plane under the magnification of 3:1, via a reflex-mirror onto a normal size instant picture cassette. Instead of the normally taken small frame colour-slide, it is now possible to expose onto special film-material an Instant-Picture and obtain with a very short time, a good photograph. This photo consists of two halves divided by a clear centerline. Each half-photograph depicts the objects as taken through the objective lens under the angle of the individual optical system.

Perfect reproduction onto each half of the picture permits immediate evaluation of the successful exposure of the photograph. By using a special viewer, this already 3 times magnified picture can be further enlarged, and simultaneously, can be looked at with a stereo effect by employing binocular objective lenses.

By the use of high quality film, the resulting picture is true to colour and the stereoscopic effect is as good as that obtained from colour-slides photographed in a similar way. A further advantage lies in the double documentation of the photograph, each half picture shows photograph of the same object and the pictures can be cut in half, given to a referring Physician or even sent by mail, without the danger of breaking. The frame, or the backside of these paper pictures is ideal for writing notes, remarks or dates. A paper picture of this kind can be easily filed in the patient's records.

The practising Gynecologist will be able when using these Instant-Pictures, to explain to the patient details of symptoms.

DESCRIPTION OF PREFERRED EMBODIMENTS

Figure 1:
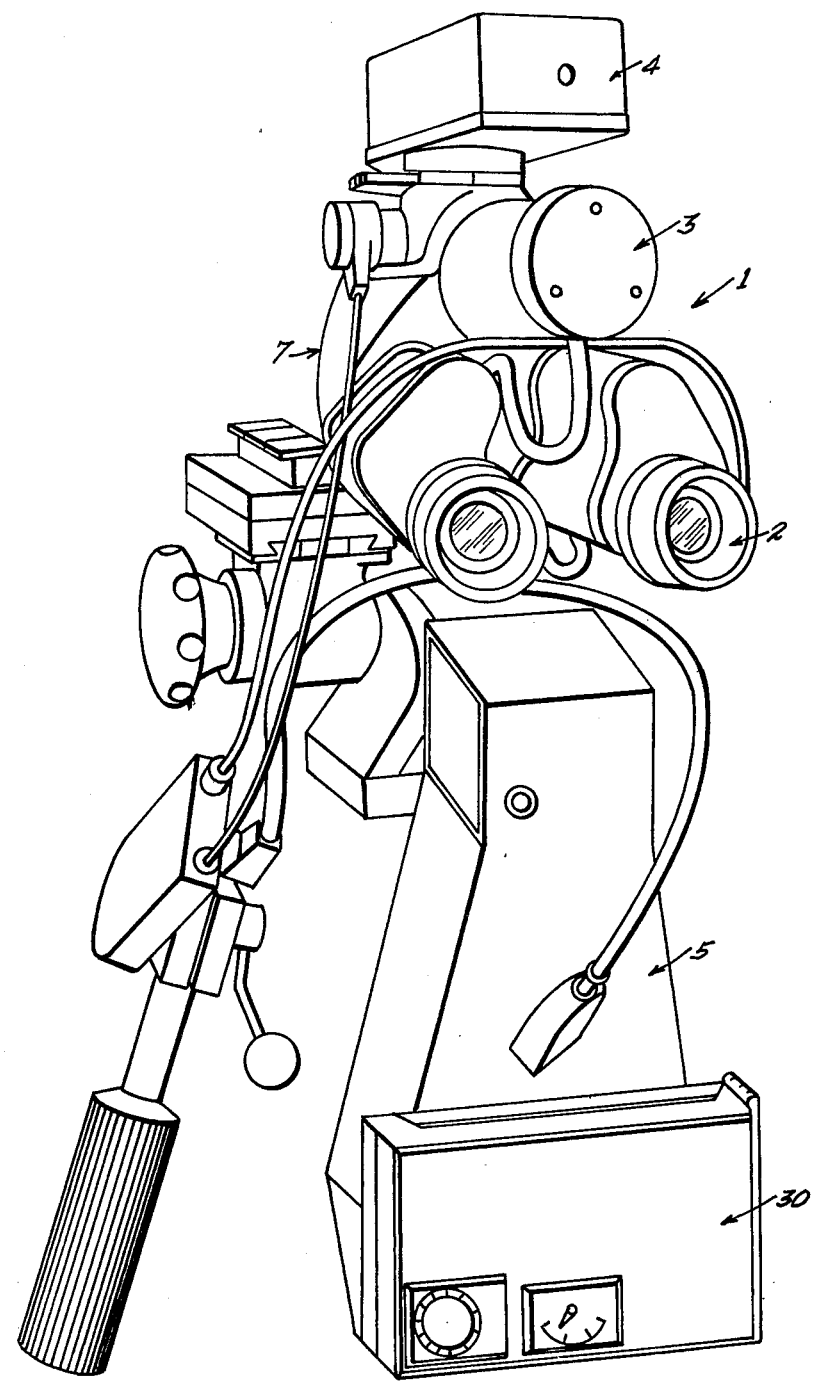
FIG. 1 is a perspective view of a Colposcope and Camera Attachment.
Figure 2:
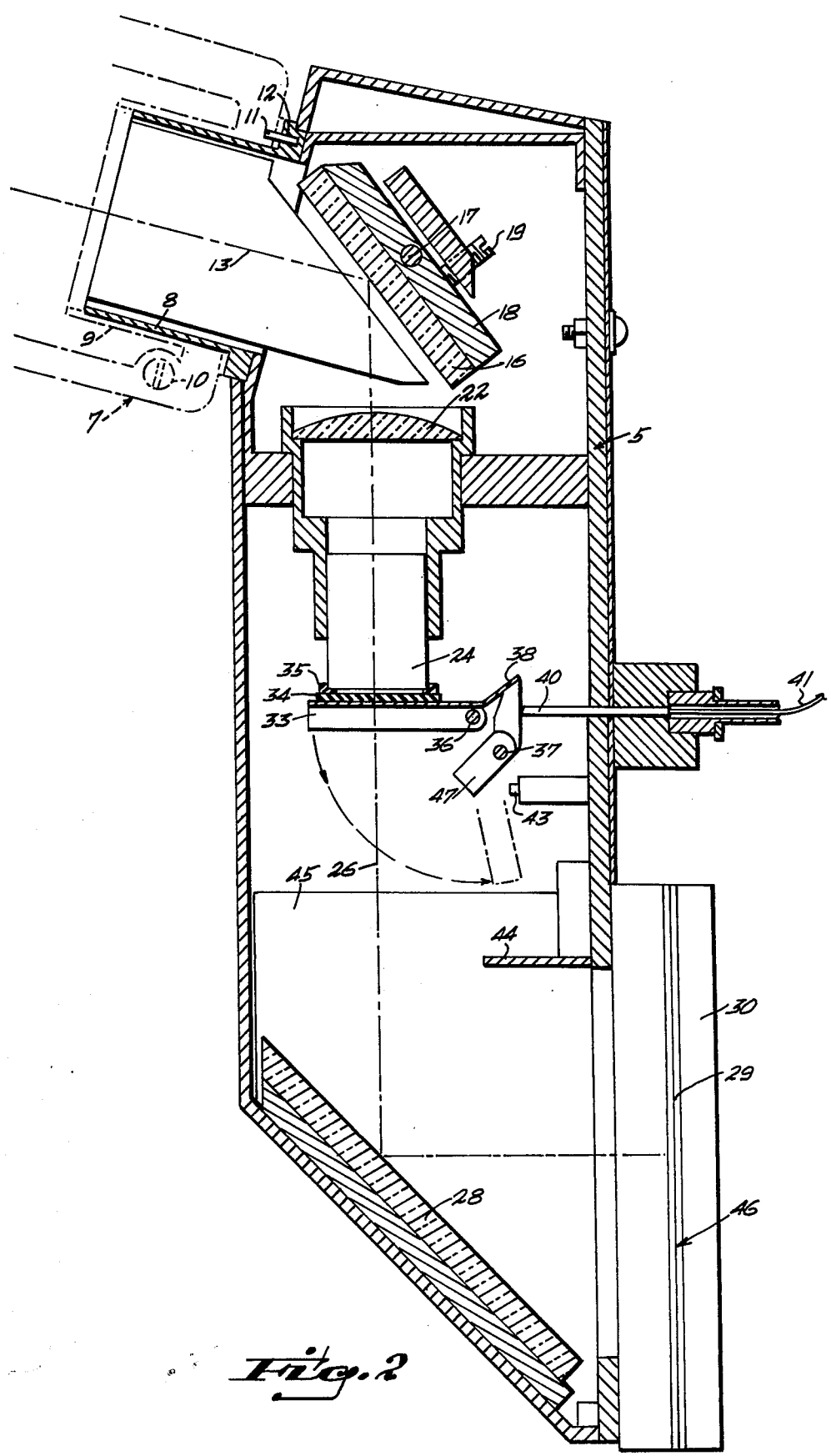
FIGS. 2 and 3 are cross-sections from two different angles.
Figure 3:
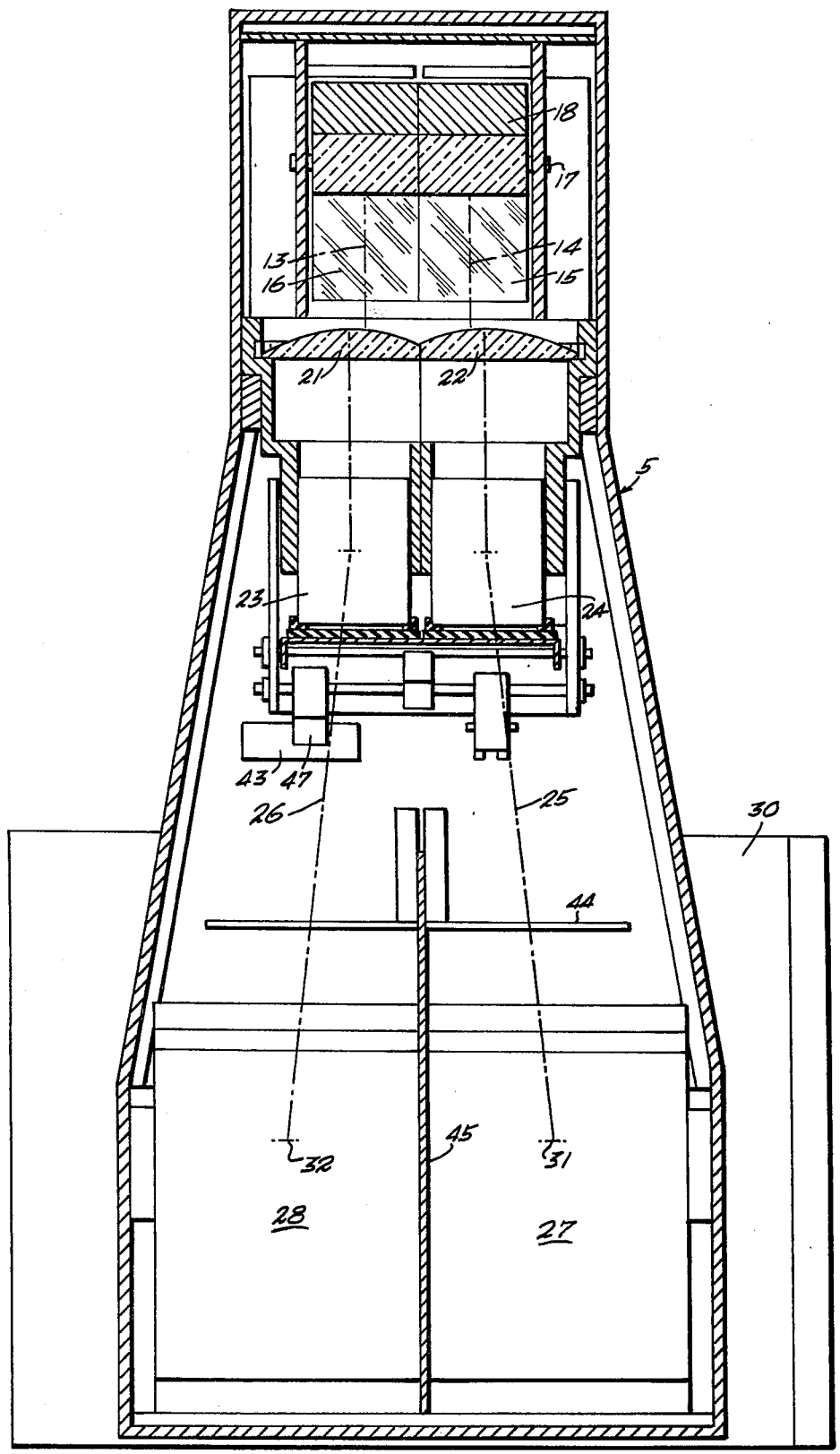

As shown in FIG. 1, the Colposcope 1 consists of the Colposcope-housing 7, two oculars 2, the light-source 3 and the additional flash-head 4. Mounted onto the Colposcope is the Photographic-Attachment 5 with the film-cassette 30.

The attachment 5 is fitted by the use of a guide tube 8 into tube 9 of the colposcope-housing 7 and held into place by the pressure of the clamping-bolt 10. A locating pin 11 fits into the slot 12 and prevents turning.

The light travels from the object through the objective lenses into the Colposcope along the optical axes 13 and 14 onto the mirrors 15 and 16, which are mounted onto the plate 18 and swings on shaft 17, permitting adjustment by the use of adjustment-screw 19 which under pressure of a spring, can be tilted to guide the light into the field objective lenses 21 and 22. The light travels further through the image relay objectives 23 and 24, to the reflex mirrors 27 and 28, onto the film 29 inside the cassette 30.

The light-beams 25 and 26, have been magnified and deflected in such a way as to transmit the focal center of the light-beams 13 and 14, onto the new centers of the pictures in 31 and 32.

The exposure is achieved by the use of a trap-shutter, where the shutter 33 with seal 34 and seal-ring 35 are fitted onto a shaft 36 and this shutter opens or closes towards the image-relay-objectives 23 and 24. The shutter is activated by a lever fitted to the shaft 37 and the angulated cam 38, when pressure exerted to the flexible cable 41 pushes the tappet 40.

Closing of the shutter is activated by releasing a spring and using the spring-tension.

When rotating the shaft 37, a lever 47 will contact the switch 43, which results in a short-circuit in the syncro-socket and causes the discharge of the flash attachments. The position of the lever is set in such a way, as to activate the switch when the trap-shutter is open.

To prevent convergence of light of the parallel running light-beams, separating wall or light-baffles 44 and 45 have been installed.

In case of using an electronically activated shutter-mechanism, another lever has been fitted and this lever engages the armature of a hub magnet by turning shaft 37 and eliminates the use of the flexible cable 41.

The film-cassette 30 contains the film-pack 46 in the photographic plane 29, which is constructed for the transport and development of an Instant-Picture process.

What is claimed is:

1. In combination, a colposcope, a photographic attachment including a film cassette, and a light source,
    said colposcope including two side-by-side occulars, an objective lens in line with each of said occulars, said lens and occulars defining a top view field of vision;
    said light source being mounted on said colposcope on a reflective line perpendicular with said field of vision;
    said photographic attachment including a tube and bushing means removably connecting the tube and said colposcope, said tube defining a predetermined line of sight parallel to said field of vision;
    said photograph attachment defining a side view field of observation wherein a specimen can be observed;
    said photographic attachment including two side-by-side adjustable reflex mirrors within said side view field of observation of said tube, whereby a bundle of light impinging upon the specimen is reflected and travels along a predetermined path of said colposcope and through said tube;
    a pair of upper reflex mirrors included in said photographic attachment spanning said tube, at a predetermined angle with respect to said line of sight through said tube, said line of sight defining an angle of incidence with respect to said reflex mirrors and an optical axis of reflection;
    two side-by-side objective field lenses arranged in perpendicular relation to said optical path; and a first and a second lower reflective mirror, each of said reflective mirrors being spaced from one of said two side-by-side objective field lenses and being arranged parallel thereto; and
    a lower reflective mirror spaced from said two side-by-side objective field lenses and said relay objective lenses at a predetermined angle with respect to said optical path defining an angle of incidence and said film cassette being arranged in spanning relation and perpendicular to the angle of reflection of said lower reflex mirror.

2. A colposcope as defined in claim 1 and including between the relay objective lenses 23 and 24 and the reflex mirrors 27 and 28, a trap shutter 33 to 35.

3. A colposcope as defined in claim 2 including a separating wall comprising a light baffle in the path for travel of the bundle of light in the range of the reflex mirrors 27, 28 and the film cassette 30.

4. A colposcope as defined in claim 3 including means supporting the field objective lenses 21 and 22 and the relay projection lenses 23, 24 in such a way, that in relation to the adjustable reflex mirrors 15, 16 the focal center of the reflex mirrors are transposed to the focal center of the field objective lenses.

5. A colposcope as defined in claim 4 wherein the film cassette 30 is equipped with instant picture film materials.

6. A colposcope as defined in claim 5 wherein the colposcope is equipped with an additional light source and means to mount the additional light source.

* * * * *